(12) United States Patent
Ramanand

(10) Patent No.: US 12,133,928 B2
(45) Date of Patent: Nov. 5, 2024

(54) PORTABLE ULTRAVIOLET DISINFECTOR

(71) Applicant: Anram Holdings, Oakville (CA)

(72) Inventor: Prakash Valentino Ramanand, Burlington (CA)

(73) Assignee: Anram Holdings, Oakville (CA)

( * ) Notice: Subject to any disclaimer, the term of this patent is extended or adjusted under 35 U.S.C. 154(b) by 0 days.

(21) Appl. No.: 18/348,652

(22) Filed: Jul. 7, 2023

(65) Prior Publication Data
US 2023/0355817 A1   Nov. 9, 2023

Related U.S. Application Data

(63) Continuation of application No. 17/674,002, filed on Feb. 17, 2022, now Pat. No. 11,730,841.
(Continued)

(51) Int. Cl.
*A61L 2/10* (2006.01)
*F21K 9/68* (2016.01)
(Continued)

(52) U.S. Cl.
CPC ........ *A61L 2/10* (2013.01); *F21K 9/68* (2016.08); *F21V 7/041* (2013.01); *G02B 19/0028* (2013.01)

(58) Field of Classification Search
CPC .... A61L 2/10; A61L 2202/11; A61L 2202/14; A61L 2202/16; F21K 9/68; F21V 7/041; G02B 19/0028; G02B 7/02
See application file for complete search history.

(56) References Cited

U.S. PATENT DOCUMENTS 3,676,667 A   7/1972   Malifaud
5,680,257 A   10/1997  Anderson
(Continued)

FOREIGN PATENT DOCUMENTS

| CN | 109973836 | 7/2019 |
| CN | 111174120 | 5/2020 |
| WO | 2019165550 | 9/2019 |

OTHER PUBLICATIONS

GIGAHERTZ-OPTIK; Halogen Lamp Light Source ISS-8P-VA; https://www.directindustry.com/prod/gigahertz-optik/product-111975-2182075.html; retrieved on Feb. 5, 2021.
(Continued)

*Primary Examiner* — Elmito Breval
(74) *Attorney, Agent, or Firm* — Rowand LLP

(57) ABSTRACT

Embodiments of the present application disclose a handheld ultraviolet (UV) apparatus for surface disinfection. In one embodiment, the handheld UV apparatus includes a cabinet, a UV lamp, and a tapered reflector unit. The cabinet includes a side having an optical window. The UV lamp is mounted within the cabinet and proximate to the optical window, where the UV lamp is configured to provide UV light through the optical window. The tapered reflector unit includes a tapered reflector mounted within a housing. The tapered reflector unit includes a first open end, a second open end, and a lumen therebetween. The first open end is attached to the side for receiving the UV light. The first open end is larger than the second open end. The tapered reflector unit is adapted for directing the UV light through the lumen towards a target surface via the second open end.

20 Claims, 9 Drawing Sheets

Related U.S. Application Data

(60) Provisional application No. 63/150,118, filed on Feb. 17, 2021.

(51) Int. Cl.
    *F21V 7/04*     (2006.01)
    *G02B 19/00*     (2006.01)

(56) References Cited

U.S. PATENT DOCUMENTS

| | | |
|---|---|---|
| 7,066,608 B2 | 6/2006 | Davis et al. |
| 7,946,735 B2 | 5/2011 | Chou et al. |
| 8,393,761 B2 | 3/2013 | Nikolaus et al. |
| 8,430,536 B1 | 4/2013 | Zhao |
| 9,265,850 B2 | 2/2016 | Davis et al. |
| 9,575,244 B2 | 2/2017 | Dhar |
| 2006/0061870 A1 | 3/2006 | Wang |
| 2008/0166175 A1 | 7/2008 | Pittel et al. |
| 2022/0062464 A1* | 3/2022 | Lyng .................... A61L 2/10 |

OTHER PUBLICATIONS

PCT International Search Report & Written Opinion dated May 3, 2022 relating to Application No. PCT/CA2022/050230.

* cited by examiner

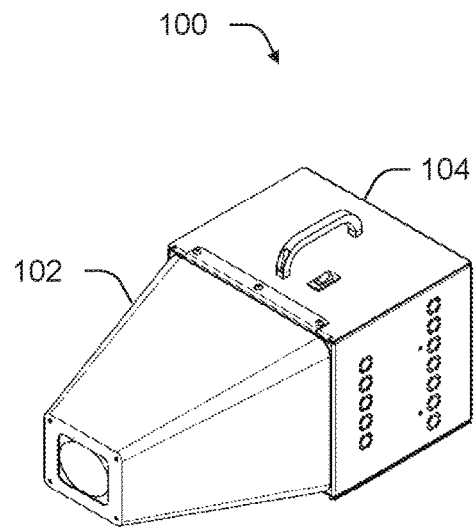
FIG. 1
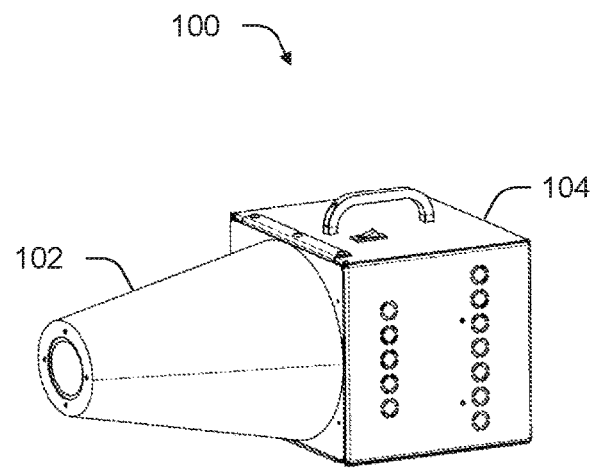
FIG. 2
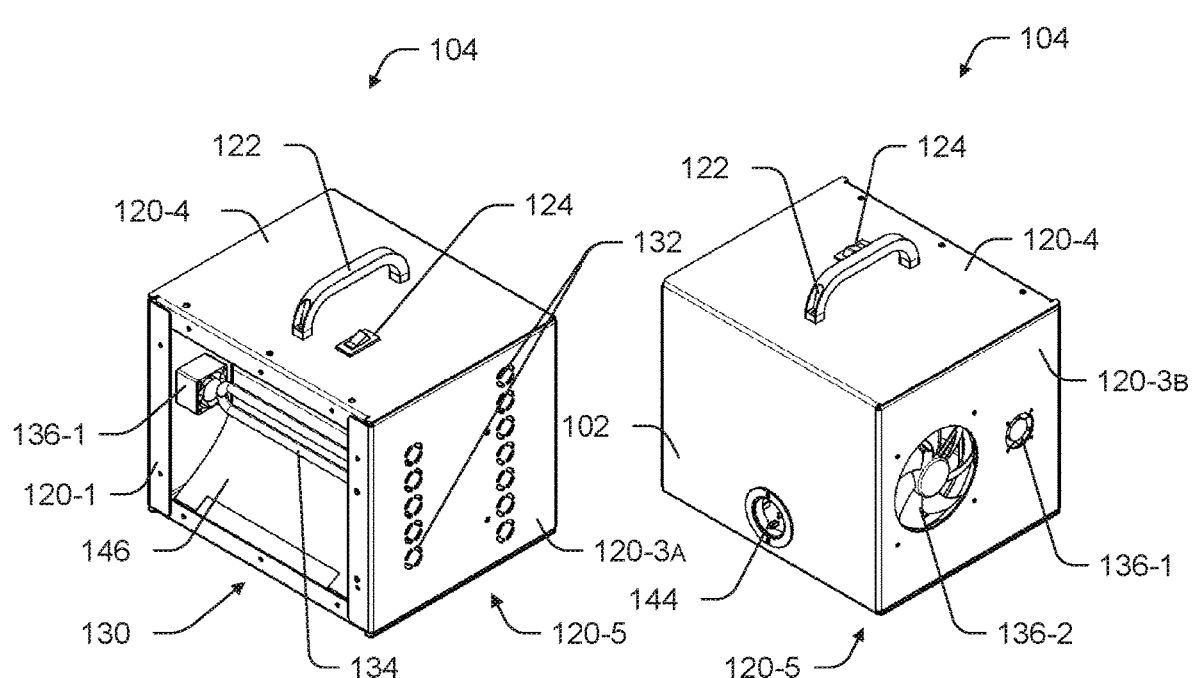
FIG. 3
FIG. 4

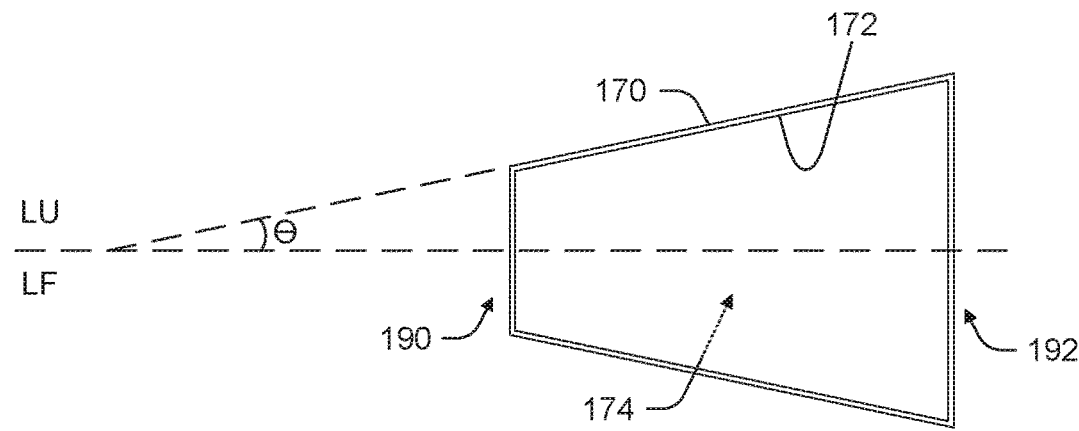
FIG. 12
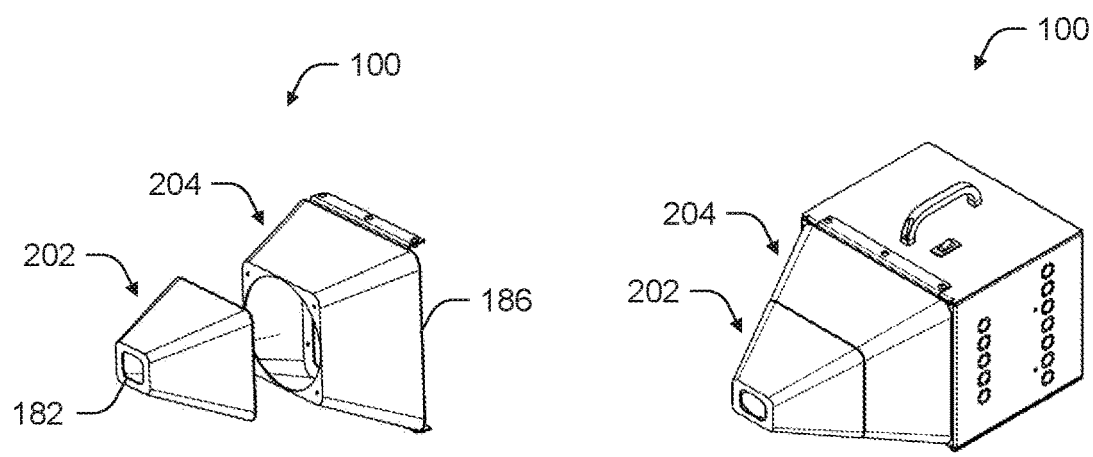
FIG. 13
FIG. 14

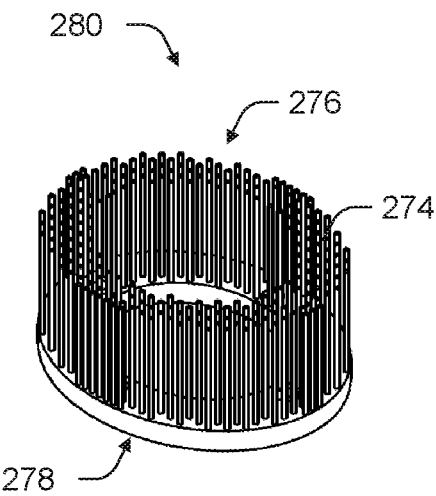 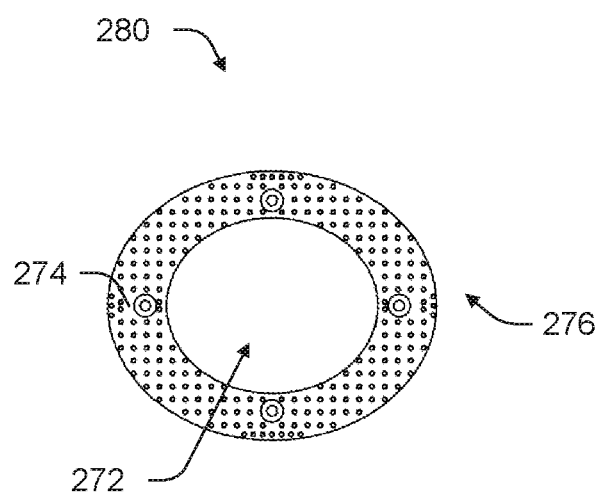
FIG. 23                FIG. 24
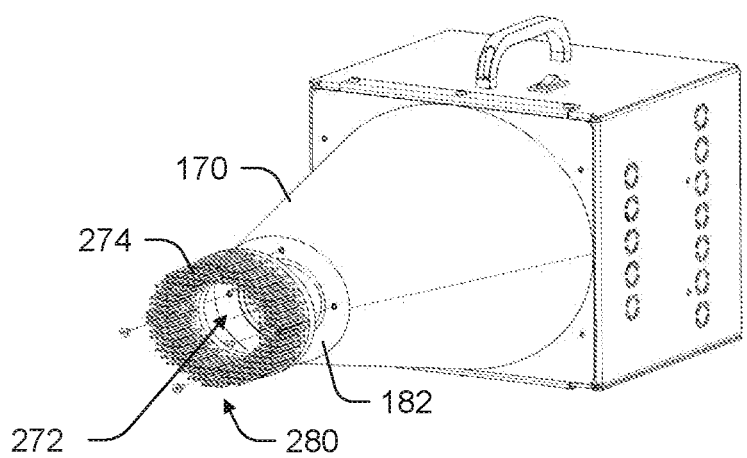
FIG. 25

PORTABLE ULTRAVIOLET DISINFECTOR

TECHNICAL FIELD

The present application generally relates to ultraviolet-based disinfection and particularly relates to portable ultraviolet disinfectors.

BACKGROUND

Ultraviolet (UV) light is an effective sterilization agent that breaks down pathogens to render them harmless. Modern disinfection devices generally include a UV source mounted on a wheeled carriage or a handheld device to project UV light for surface disinfection. Such traditional wheeled UV devices typically allow for UV irradiation only in elevated or set planes to fail in disinfecting hidden or obstructed high-touch surfaces, for example, room corners and undersides of doorknobs and handrails. In contrast, handheld UV devices provide better maneuverability for targeting such surfaces. However, conventional handheld UV devices typically rely on complicated and expensive software or electronic manipulation to improve the disinfection efficiency and provide no measures to limit UV dispersion away from a target surface.

SUMMARY

Embodiments of the present application describe a portable ultraviolet (UV) disinfector. One embodiment of the portable UV disinfector includes a handheld UV apparatus for surface disinfection. The handheld UV apparatus includes a cabinet, a UV lamp, and a tapered reflector unit. The cabinet includes a side having an optical window. The UV lamp may be mounted within the cabinet and proximate to the optical window. The UV lamp may be configured to provide UV light through the optical window. The tapered reflector unit may include a tapered reflector mounted within a housing. The tapered reflector unit may include a first open end, a second open end, and a lumen therebetween. The first open end may be attached to the side for receiving the UV light. The first open end may be larger than the second open end. The tapered reflector unit may be adapted for directing the UV light through the lumen towards a target surface via the second open end.

Another embodiment of the portable UV apparatus includes a handheld ultraviolet (UV) apparatus for surface disinfection, where the handheld UV apparatus includes a cabinet, a UV lamp, a housing, and a frustoconical reflector. The cabinet may include a side having an optical window. The UV lamp may be mounted within the cabinet and proximate to the optical window. The UV lamp may be configured to provide UV light through the optical window. The housing may include a distal portion and a proximal portion including a proximal open end. The housing may taper from the proximal open end to a distal open end of the distal portion, where the proximal open end may be attached to the side. The frustoconical reflector may be mounted within the housing. The frustoconical reflector may include a distal opening located in the distal portion and an opposing proximal opening located in the proximal portion. The proximal opening may be adapted to receive the UV light and have a first diameter greater than a second diameter of the distal opening. The frustoconical reflector may be adapted for directing the received UV light therethrough towards a target surface via the distal opening.

The above summary of exemplary embodiments is not intended to describe each disclosed embodiment or every implementation of the present application. Other and further aspects and features of the application will be evident from reading the following detailed description of the embodiments, which are intended to illustrate, not limit, the present application.

BRIEF DESCRIPTION OF DRAWINGS

The illustrated embodiments of the subject matter will be best understood by reference to the drawings, wherein like parts are designated by like numerals throughout. The following description is intended only by way of example, and simply illustrates certain selected embodiments of devices, systems, and processes that are consistent with the subject matter as described herein.

FIG. 1 is a front perspective view of an exemplary portable UV disinfector, according to an embodiment of the present application.

FIG. 2 is a front perspective view of the portable UV disinfector of FIG. 1 mounted with a frustoconical tapered reflector unit, according to another embodiment of the present application.

FIG. 3 is a front right perspective view of a cabinet for the portable UV disinfector of FIG. 1, according to an embodiment of the present application.

FIG. 4 is a rear left perspective view of the cabinet of FIG. 3, according to an embodiment of the present application.

FIG. 12 is a side elevation view of the tapered reflector unit of FIG. 10 showing the frustoconical reflector of FIG. 8 inside a housing, according to an embodiment of the present application.

FIG. 13 is a front right perspective view of a tapered reflector unit made up of two distinct parts, according to another embodiment of the present application.

FIG. 14 is a front right perspective view of a portable UV disinfector mounted with the tapered reflector unit of FIG. 13, according to an embodiment of the present application.

FIG. 23 is a front left perspective view of an exemplary round brush for the portable UV disinfector of FIG. 1, FIG. 2, FIG. 14, and FIG. 16, according to an embodiment of the present application.

FIG. 24 is a top elevation view of the round brush of FIG. 23, according to an embodiment of the present application.

FIG. 25 is a front right perspective view of the portable UV disinfector of FIG. 1 showing the round brush of FIG. 23 being mounted thereon, according to an embodiment of the present application.

DETAILED DESCRIPTION

Figures 5, 6:
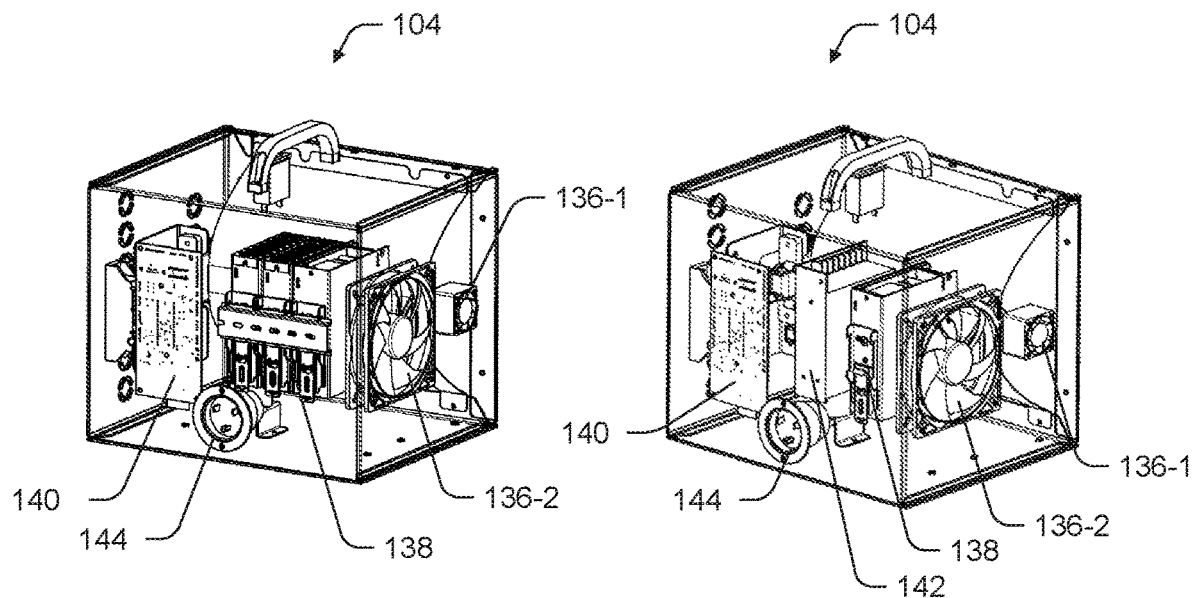
FIG. 5 is a rear right perspective view of the cabinet of FIG. 3 showing internal components, according to an embodiment of the present application.
FIG. 6 is a rear right perspective view of the cabinet of FIG. 3 including a battery for the portable UV disinfector of FIG. 1, according to an embodiment of the present application.

The following detailed description is provided with reference to the drawings herein. Exemplary embodiments are provided as illustrative examples so as to enable those skilled in the art to practice the application. It will be appreciated that further variations of the concepts and embodiments disclosed herein can be contemplated. The examples described in the present application may be used together in different combinations. In the following description, details are set forth in order to provide an understanding of the present application. It will be readily apparent, however, that the present application may be practiced without limitation to all these details. Also, throughout the present application, the terms "a" and "an" are intended to denote at least one of a particular element. The terms "a" and "an" may also denote more than one of a particular element. As used herein, the term "includes" means includes but not limited to, the term "including" means including but not limited to. The term "based on" means based at least in part on, the term "based upon" means based at least in part upon, and the term "such as" means such as but not limited to. The term "relevant" means closely connected or appropriate to what is being done or considered.

Further, where certain elements of the present application can be partially or fully implemented using known components, only those portions of such known components that are necessary for an understanding of the present application will be described, and detailed descriptions of other portions of such known components are omitted so as not to obscure the invention(s). In the present application, an embodiment showing a singular component should not be considered limiting; rather, the present application is intended to encompass other embodiments including a plurality of the same component, and vice-versa, unless explicitly stated otherwise herein. Moreover, the applicant does not intend for any term in the present application to be ascribed an uncommon or special meaning unless explicitly set forth as such. The present invention encompasses present and future known equivalents to the known components referred to herein by way of illustration or description.

Embodiments are disclosed in the context of surface disinfection and optical or light amplification; however, one having ordinary skill in the art would understand that the concepts described in the present application may be implemented for various other applications including, but are not limited to, UV curing, air or water purification, light-based communication, indoor gardening, and fluorescent inspection or investigation.

FIG. 1 is a front perspective view of an exemplary portable ultraviolet (UV) disinfector 100, according to an embodiment of the present application. The portable UV disinfector 100 (or simply, disinfector 100) may represent a wide variety of portable and/or handheld devices configured to emit UV light for disinfection. In one embodiment, the disinfector 100 may include a tapered reflector unit 102 and a cabinet 104. The tapered reflector unit 102 may assist in improving the uniformity and/or intensity of the UV light passing therethrough. The tapered reflector unit 102 may be constructed to have any suitable shapes known in the art. For example, as illustrated in FIG. 1, the tapered reflector unit 102 may be shaped as a pyramidal frustum. In another example (FIG. 2), the tapered reflector unit 102 may be frustoconical, i.e., shaped as a conical frustum. Other examples may include the tapered reflector unit 102, or components thereof, being shaped as a combination of a conical frustum and a polygonal frustum such as a pyramidal frustum. The tapered reflector unit 102 and the cabinet 104 may be constructed separately for an ease of manufacturing and then assembled together.

The cabinet 104 may have any suitable geometry, cross-section, partition(s), and/or compartment(s) for carrying various components for providing or generating a germicide such as the UV light. The cabinet 104 may be formed as a single part or a set of multiple separate parts (e.g., panels, compartments, containers, etc.) assembled together. For example, as illustrated in FIGS. 3-6, the cabinet 104 may include a front plate 120-1, a rear plate 120-2, a first lateral plate 120-3a, a second lateral plate 120-3b, a top plate 120-4, and a bottom plate 120-5 (hereinafter collectively referred to as plates 120). Each of the first lateral plate 120-3a and the second lateral plate 120-3b (hereinafter collectively referred to as lateral plates 120-3) may extend between the front plate 120-1 and the rear plate 120-2. In the illustrated embodiment, the top plate 120-4 may include a handle 122 being permanently attached, removably secured, or formed integral to the cabinet 104. Some examples may include the handle 122 being a portion or body design of the cabinet 104, or the disinfector 100, usable for assisting an operator in holding, carrying, and/or moving the disinfector 100, and/or the cabinet 104. Other examples may include any of the plates 120 including one or more interactive units to assist in (i) controlling, activating, terminating, detaching and/or attaching a component such as a UV source or an intended operation of the disinfector 100 and/or (ii) providing an indication (e.g., audio, visual, haptic, etc.) in response thereof. For instance, as illustrated, the top plate 120-4 may include a switch 124 to turn on and off the disinfector 100 or a part thereof such as the UV source or lamp. Other examples of the interactive units may include, but are not limited to, display units, buttons, rotary dials, sensors, microphones, speakers, cameras, interactive touchscreens, and lighting elements such as bulbs and light emitting diodes (LEDs). Further, the front plate 120-1 may include a window 130 made optically permeable to at least the UV light. In one example, the window 130, or the corresponding plate such as the front plate 120-1, may include, or be mounted with, a quartz glass or any other suitable materials known in the art that may be optically permeable to UV light and assist in protecting components inside the cabinet 104 from dust. In another example, the window 130 may include one or more openings. Other examples may include the window 130 being alternatively, or additionally, mounted with an optical filter configured for allowing the UV light, or a specific wavelength thereof or that of electromagnetic radiation, to pass therethrough. The window 130 may have a circular shape, an elliptical shape, a polygonal shape (e.g., rectangular, square, trapezoid, etc.), or any combinations thereof. The window 130 may be located in the front plate 120-1; however, some examples may include the window 130 being additionally, or alternatively located, in any other plates 120 depending on an intended application and/or connection with a functional part such as or including the tapered reflector unit 102.

Each of the plates 120 may correspond to a side of the cabinet 104. The plates 120, or the cabinet 104, may be made of metals, polymers, alloys, or any other suitable materials known in the art that are sufficiently rigid, sturdy, and opaque to (i) support various operational components of the disinfector 100 and (ii) block UV light. One or more of the lateral plates 120-3, such as the first lateral plate 120-3a, may have vent openings 132 for allowing air to pass therethrough. The vent openings 132 may assist in dissipating heat from in and around the cabinet 104 during operation. In some examples, the vent openings 132 may be constructed or supplemented with additional components, such as downward slanting panels (not shown), to limit or prevent misdirected projection and/or leakage of UV light therefrom to the ambient surroundings while allowing airflow.

In one embodiment, the cabinet 104 may include a UV source such as a UV lamp 134, a cooling unit, and a control system. The UV source may include any high voltage optical component (e.g., Xenon UV lamp, UV bulb, etc.) or low voltage optical component (e.g., UV LED), or any combinations thereof. In the illustrated example, the UV source may be an elongated UV lamp 134 configured to emit UV light of a predetermined energy within a predetermined germicidal wavelength range or wavelengths including 280 nm (i.e., UV type C); 280-315 nm (i.e., UV type B); 200-300 nm (i.e., middle UV); and 122-200 nm (i.e., far UV), or any combinations thereof. Other wavelength ranges may also be employed, including those providing ionizing radiation (e.g., extreme UV having a wavelength between 10-120 nm).

The UV lamp 134 may be a pulsed radiation source, a continuous radiation source, or a set of both the pulsed radiation source and the continuous radiation source configured to emit pulses of UV light. In some examples, the UV lamp 134 may be configured for pulsed or near continuous emission of the UV light. Other examples may include the UV lamp 134 operating in combination with different types of radiation and non-radiation sources (not shown), which may be provided on the disinfector 100, or the cabinet 104, and configured for providing assistive agents for disinfection. Examples of such assistive agents may include, but are not limited to, chemical agents (e.g., alcohols, oxidizing agents, naturally occurring or modified compounds, etc.), physical agents (e.g., heat, pressure, vibration, sound, radiation, plasma, electrical current, etc.), and biological agents (e.g., organisms, plants or plant products, organic residues, assistive-pathogens, etc.). In some embodiments, the UV lamp 134 may be partitioned from other components within the cabinet 104. For example, the UV lamp 134 may be housed within a dedicated casing or compartment.

The UV lamp 134 may be mounted within the cabinet 104 and positioned adjacent to the window 130. The UV lamp 134 may be arranged vertically, horizontally, or at an angle relative to a longitudinal axis LU of the tapered reflector unit 102. For instance, as illustrated, the UV lamp 134 may be mounted to the first lateral plate 120-3a and inside the cabinet 104. The mounted UV lamp 134 may be arranged horizontally and parallel to the bottom plate 120-5, so that the UV lamp 134 extends perpendicular to the longitudinal axis LU of the tapered reflector unit 102 upon being attached. The cabinet 104 may further include a parabolic reflector 146 behind the UV lamp 134. The parabolic reflector 146 may assist in directing the UV light towards the window 130. The UV lamp 134 may be cooled by the cooling unit during operation.

In one embodiment, the cooling unit may include a first fan 136-1 and a second fan 136-2 (hereinafter collectively referred to as fans 136) for dissipating heat accumulated around the components or portions connected to the cabinet 104. For example, as illustrated, the fans 136 may be mounted to the second lateral plate 120-3b; however, any other plates 120 may also be contemplated for mounting one or more fans such as the fans 136. The first fan 136-1 may be mounted along a longitudinal axis of the UV lamp 134. The first fan 136-1 may operate as a vacuum source for drawing out warm air and creating a negative pressure within the cabinet 104 for cooling the UV lamp 134 and surrounding components. In some instances, the first fan 136-1, or the vacuum source, may be optionally implemented using channeling devices such as hoses (not shown) extending to specific locations or components (e.g., UV lamp 134, control system, etc.) of the cabinet 104 or the disinfector 100. On the other hand, the second fan 136-2 may blow air, thereby creating a positive airflow, inside the cabinet 104. Such positive airflow may cool the surrounding components, such as the UV lamp 134, by pushing out the warm air through the vent openings 132. The UV lamp 134 and other electrical/electronic components of the disinfector 100 may be driven by the control system.

The control system may include a power supply unit 138 and a controller 140. The power supply unit 138 may include or be coupled to a high voltage power supply, a low voltage power supply, or a combination thereof. For instance, the power supply unit 138 may deliver the required power supply from an external electrical outlet via a power cord (not shown) attached to a socket 144 in the rear plate 120-2 of the cabinet 104. In another instance, as shown in FIG. 6, the power supply unit 138 may additionally include a battery 142 placed within the cabinet 104. The socket 144, in this instance, may operate as a power connector to power standalone devices and components. The power connector may be configured to operate independently, or in combination with the UV lamp 134. Further, the controller 140 may include an electronic or an electromechanical device configured to control predefined or dynamically defined functions of various components operationally coupled to the disinfector 100. The controller 140 may be implemented by way of a single device (e.g., a computing device, processor or an electronic storage device) or a combination of multiple devices. In some embodiments, the controller 140 may be implemented in hardware or a suitable combination of hardware and software. In some examples, the controller 140 may operate in communication with a computing device or a sensor located locally or remote from the cabinet 104, or the disinfector 100. In FIG. 5 and FIG. 6, the cabinet 104 is shown to include transparent sides or plates 120 only for the sake of explaining the components located therewith. One having ordinary skill in the art would understand that walls of the cabinet 104, or related components such as plates 120, would be made optically impermeable to UV light based on concepts disclosed in the present application.

The cabinet 104, or a part thereof, may be permanently attached, detachably secured, or formed integral to the tapered reflector unit 102 or a portion thereof. For instance, the tapered reflector unit 102 may have a first portion 150 (or proximal portion), a second portion 152 (or distal portion), and a tapered section 158 extending therebetween. In the present disclosure, a term "proximal" may refer to a portion, section, side, end, location, direction, or position being relatively closest to the window 130 of the cabinet 104 102 and/or the UV lamp 134. On the other hand, a term "distal" may refer to a portion, section, side, end, location, direction, or position being relatively farthest from the window 130 of the cabinet 104 and/or the UV lamp 134.

Figure 7:
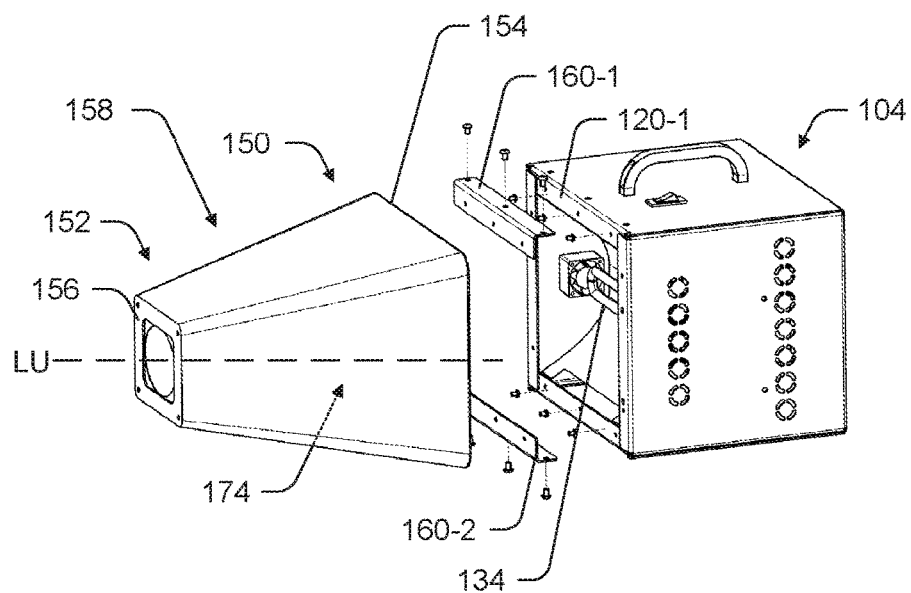
FIG. 7 is a front right perspective view of the portable UV disinfector of FIG. 1 including a tapered reflector unit, the cabinet of FIG. 3, and L-shaped angle bars therebetween, according to an embodiment of the present application.

The tapered reflector unit 102, or the first portion 150, may have a first open end 154 having a first cross-sectional dimension. Similarly, the tapered reflector unit 102, or the second portion 152, may have a second open end 156 having a second cross-sectional dimension. In the present application, an "open end" is used in the context of its broadest definition. For example, the "open end" may refer to or include a surface including an opening. In some examples, the "open end" may refer to a surface including an opening in optical communication with another opening. The first open end 154 may be located opposite to the second open end 156 along a longitudinal axis LU of the tapered reflector unit 102. The tapered section 158 may gradually taper from the first open end 154 to the second open end 156 such that the first cross-sectional dimension may be relatively greater than the second cross-sectional dimension. In one example, the second open end 156, or the second cross-sectional dimension, may be at least approximately 20% smaller than the first open end 154, or the first cross-sectional dimension. The tapered section 158 may be shaped as a pyramidal frustum; however, other examples may include the tapered section 158 being shaped to have a circular cross-section, an elliptical cross-section, a polygonal cross-section (e.g., square, rectangular, or trapezoidal cross-sections, etc.) or any combinations thereof. For instance, the tapered section 158 may have a shape of a pyramidal frustum having a square cross-section or a frustoconical shape having a circular cross-section. As shown in FIG. 7, the tapered section 158 may include a lumen 174 for allowing the UV light to pass therethrough. In some examples, the tapered section 158 may be hollow. The lumen 174 have any suitable shape depending a shape of the tapered section 158. In one instance, the lumen 174 may be frustoconical based on the tapered section 158, or the tapered reflector unit 102, having a frustoconical shape. Other instances may include the lumen 174 being shaped as a pyramidal frustum, or any similar polygonal frustum.

Figure 8:
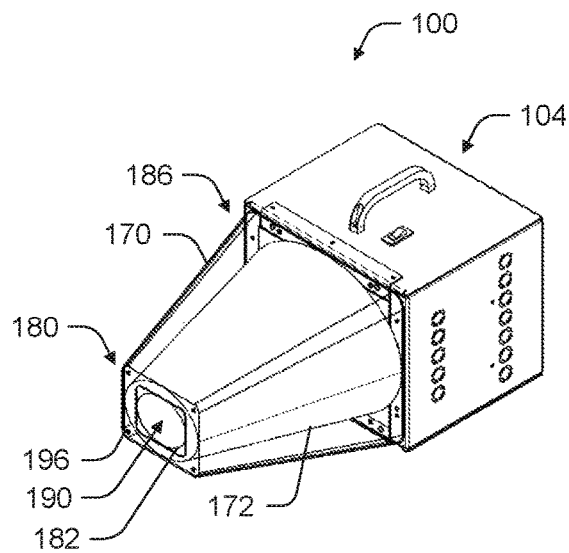
FIG. 8 is a front right perspective view of the portable UV disinfector of FIG. 1 showing a frustoconical reflector inside a tapered reflector unit, according to an embodiment of the present application.

In one embodiment, as illustrated in FIG. 7, the tapered reflector unit 102 may be detachably secured to the front plate 120-1 via L-shape angle bars 160-1 and 160-2 connected using nuts and bolts. Other examples may include the tapered reflector unit 102 being detachably secured using any other suitable connection types (e.g., screws, luer lock, plug and socket, latch lock, etc.) or connection mechanisms (e.g., screw fit, snap fit, welding, gluing, etc.) known in the art. Upon being secured to the front plate 120-1, the tapered reflector unit 102 may be disposed in front of the window 130, or the UV lamp 134, unlike the parabolic reflector 146. The tapered reflector unit 102 may be made up of multiple pieces or a single piece based on (i) a type or arrangement of underlying reflector(s), (ii) ease of construction and/or assembly, (iii) ease of handling and/or portability of the disinfector 100. In one embodiment, as illustrated in FIG. 8, the tapered reflector unit 102 may include a tapered housing 170 and a tapered reflector 172 mounted within the housing 170. The tapered reflector 172 may be mounted within the tapered housing 170 using any suitable connection mechanisms known in the art including those mentioned above. The tapered reflector 172 may have a frustoconical shape (e.g., having a circular cross-section) and the tapered housing 170 may be shaped as a pyramidal frustum, e.g., having a square cross-section; however, other examples may include the housing 170 and the tapered reflector 172 having the same longitudinal shapes or the same cross-sectional shapes. For instance, the tapered reflector 172 may have a frustoconical shape within a frustoconical housing 170. Other instances may include the tapered reflector 172 being shaped as a pyramidal frustum within the housing 170 having the same shape.

The tapered reflector 172 (e.g., frustoconical reflector) may be substantially hollow, or include a lumen 176, for allowing the light to pass therethrough. Some examples may include the tapered housing 170 having an inner surface (not shown) operating as a reflector and extending longitudinally along the tapered section 158. For instance, the inner surface may be reflective (e.g., inner surface made of a reflective metal or alloy) or made reflective, e.g., upon being coated with any suitable optically reflective inks or paints known in the art. The inner surface, in some examples, may be curved; however, other examples may include the inner surface being or including a flat surface. Accordingly, in these examples, the housing 170 may be substantially hollow for allowing the light to pass therethrough and the inner surface operating as the tapered reflector 172, and/or the lumen 176, may be shaped same as the housing 170.

Figure 9:
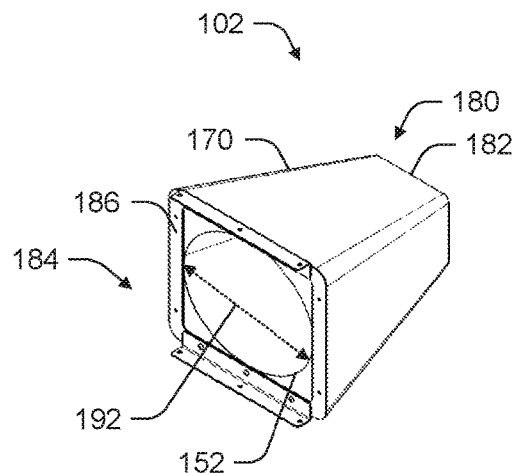
FIG. 9 is a rear right perspective view of the tapered reflector unit of FIG. 8 with L-shaped angle bars of FIG. 7, according to an embodiment of the present application.
Figure 10:
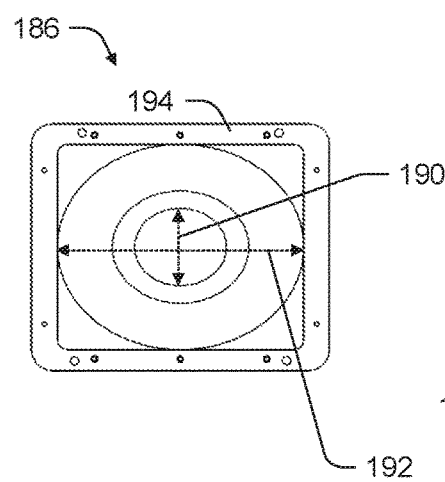
FIG. 10 is a rear elevation view of the tapered reflector unit of FIG. 9 without the L-shaped angle bars of FIG. 7, according to an embodiment of the present application.

The housing 170, as shown in FIGS. 8-10, may include a distal portion 180 having a distal open end 182 and a proximal portion 184 including a proximal open end 186. The proximal open end 186 may include the first open end 154 of the tapered reflector unit 102 and the distal open end 182 may include the second open end 156 of the tapered reflector unit 102. In some examples, the distal open end 182, or the second open end 156, may extend in a plane (hereinafter referred to as tip plane) intersecting the longitudinal axis LU of the tapered reflector unit 102. The tip plane may be perpendicular, or at an angle of 90 degrees, with respect to the longitudinal axis LU of the tapered reflector unit 102; however, some examples may include the angle being less than or greater than 90 degrees for imparting a tapered profile to the distal open end 182. The tip plane (e.g., second open end 156 or the distal open end 182) may be parallel to a base plane including the proximal open end 186 (or the first open end 154); however, other examples may include the tip plane being non-parallel to the base plane. The housing 170 may be tapered between the proximal open end 186 and the distal open end 182. The housing 170 may include the tapered reflector 172 mounted therein. The tapered reflector 172 may have a distal opening 190 in the distal portion 180 and a proximal opening 192 in the proximal portion 184. The proximal opening 192 may be located proximate to the proximal open end 186 and the distal opening 190 may be located proximate to the distal open end 182 of the housing 170. In some examples, the proximal open end 186 may include the proximal opening 192 and the distal open end 182 may include the distal opening 190.

Figure 11:
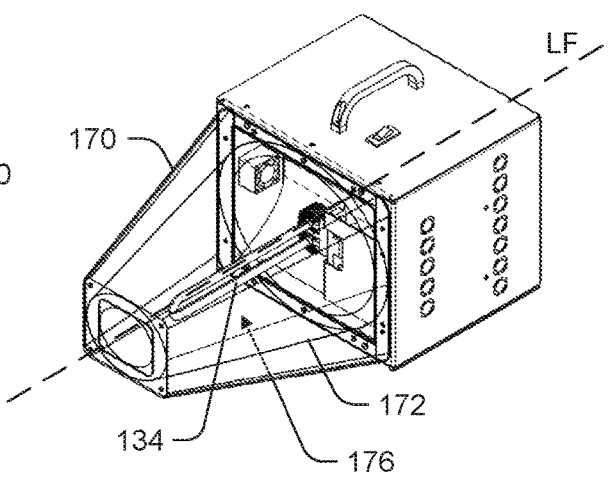
FIG. 11 is a front right perspective view of the portable UV disinfector of FIG. 1 showing a UV lamp extending into the frustoconical reflector of FIG. 8, according to an embodiment of the present application.

As illustrated in FIG. 10, the proximal open end 186 may include a rim (or a first periphery 194) of the housing 170. Similarly, the distal open end 182 may have a second periphery 196. The rim, or the proximal open end 186, may be attached to the front plate 120-1 of the cabinet 104 using any suitable connection mechanisms as discussed above. Upon being attached, the proximal open end 186, and/or the proximal opening 192, may substantially align with and cover the window 130 in the front plate 120-1 of the cabinet 104 to avoid any light leakage from any spaces between the cabinet 104 and the tapered reflector unit 102 or the housing 170. Some examples may include the UV lamp 134 being mounted within the cabinet 104 but extending into the attached tapered reflector unit 102, or the underlying tapered reflector 172, as shown in FIG. 11. The UV lamp 134 may extend parallel to the longitudinal axis LF of the tapered reflector 172, or that of the tapered reflector unit 102.

The proximal opening 192 may have a first diameter and the distal opening 190 may have a second diameter. In one example the first diameter (or the first periphery 194) may be at least approximately 20% larger than the second diameter (or the second periphery 196). The second diameter may range from approximately 5 cm to approximately 30 cm depending on the intended size of the disinfector 100 and intended coverage for surface disinfection. As illustrated in FIG. 12, the proximal opening 192 may be located opposite to the distal opening 190 along the longitudinal axis LU of the tapered reflector unit 102, or that of the tapered reflector 172. The longitudinal axis LU of the tapered reflector unit 102, or that of the tapered reflector 172 in some examples, may define, or include, a central axis of the window 130, the front plate 120-1, or the cabinet 104. The central axis may be perpendicular to the front plate 120-1, or the window 130, in one example. The central axis may also longitudinally pass through the respective centers of the proximal opening 192 and the distal opening 190; however, the central axis being off-centered from the respective centers of the proximal opening 192 and the distal opening 190 may also be contemplated.

Further, a length of the tapered reflector 172, or that of the tapered reflector unit 102, may be inversely proportional to a respective conical half angle. For example, as illustrated in FIG. 12, a first conical half angle θ of the tapered reflector unit 102 may refer to an angle between a tapered surface, e.g., of the housing 170, and the longitudinal axis LU of the tapered reflector unit 102. Similarly, a second conical half angle ϕ of the tapered reflector 172 may refer to an angle between a tapered surface, e.g., of the tapered reflector 172, and the longitudinal axis LF of the tapered reflector 172 such as the frustoconical reflector. Each of the first conical half angle and the second conical half angle (hereinafter collectively referred to as conical half angles) may be proportional to each other. Each of the conical half angles may range from approximately 15 degrees to approximately 75 degrees. Greater the conical half angle, shorter the length of the respective component. In one example, a total length of the housing 170, or the tapered reflector unit 102, along the longitudinal axis, LU or LF, may be up to approximately 20% greater than that of the tapered reflector 172. In another example, the tapered reflector 172 may have a total length along its longitudinal LF axis ranging from approximately 10 cm to approximately 90 cm.

The tapering of the reflector, such as the tapered reflector 172, may assist in (i) improving the intensity and/or uniformity of light passing therethrough, or exiting therefrom, due to total internal reflection (TIR), and (ii) increasing a range or coverage of the UV light exiting from the tapered reflector unit 102. The intensity of light may be further augmented by the curved profile of the tapered reflector 172 having a circular cross-section; however, other suitable cross-sections including, but not limited to, rectangular, square, and polygonal, or any combinations thereof, may also be contemplated. In some other examples, at least inner surfaces of the tapered reflector 172, or the housing 170, may be additionally made textured to further augment TIR and hence, the intensity and/or uniformity of the UV light emitted on to a target surface from or via the distal open end 182, or the distal opening 190. In a first example, the tapering feature of the tapered reflector 172 alone may provide a range of UV light, or the disinfector 100, of at least approximately 1 meter at a pulse rate of approximately 10 and 50 pulses per second and preset energy per pulse based on the tapered reflector 172 having a minimum length of 30 cm. The range may refer to a distance between the distal opening 190 and a target surface. In the first example, the energy received at the target surface approximately 1 meter away from the distal opening 190 may be between approximately 10 and 120 joules of UV energy. In a second example, the tapering feature of tapered reflector 172 in combination with textured surface may provide the range of at least approximately 1.5 meters at the same pulse rate and energy per pulse based on the tapered reflector 172 having a minimum length of at least approximately 30 cm. In the second example, the energy received at the target surface approximately 1.5 meters away from the distal opening 190, may increase by at least approximately 3% up to approximately 15% of the energy received at the 1 meter distance without the textured surface.

In a second embodiment, the tapered reflector unit 102 may be made up of multiple parts. For example, as illustrated in FIG. 13, the tapered reflector unit 102 may be made up a front distal portion 202 (hereinafter referred to as front portion 202) and a rear proximal portion 204 (hereinafter referred to as rear portion 204) manufactured separately and assembled together. Each of the front portion 202 and the rear portion 204 may include a respective tapered housing 170 and a respective tapered reflector 172 (e.g., frustoconical reflector) including a lumen such as the lumen 176 for allowing the UV light to pass therethrough, as described above. The front portion 202 may include the distal open end 182 and a rear open end. Similarly, the rear portion 204 may include a front open end and the proximal open end 186, which may be attached to the front plate 120-1 as discussed above. The rear open end may be detachably secured to the front open end using any suitable connection mechanisms known in the art including those mentioned above, as illustrated in FIG. 14, to avoid any light leakage.

Figure 15:
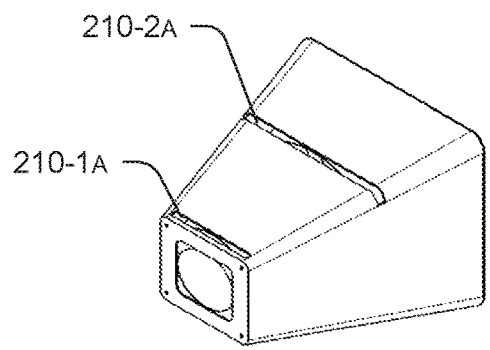
FIG. 15 is a front right perspective view of a tapered reflector unit including slots, according to an embodiment of the present application.
Figure 16:
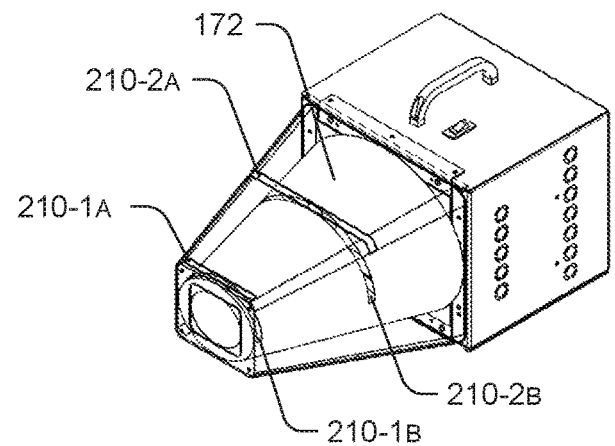
FIG. 16 is a front right perspective view of a portable UV disinfector mounted with the tapered reflector unit of FIG. 15 including a slotted frustoconical reflector, according to an embodiment of the present application.
Figure 17:
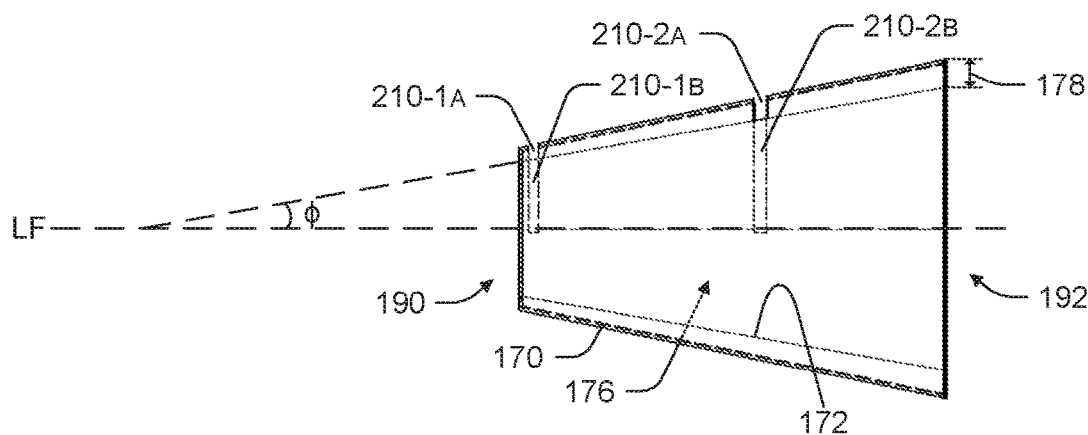
FIG. 17 is a side elevation view of the tapered reflector unit of FIG. 15 showing the slotted frustoconical reflector of FIG. 16 inside a slotted housing, according to an embodiment of the present application.

In a third embodiment, as illustrated in FIGS. 15-17, the tapered reflector unit 102 may include one or more slots for receiving a first attachment. For example, the housing 170 may include a first front slot 210-1a and a first rear slot 210-2a (hereinafter collectively referred to as housing slots 210-a). Similarly, the tapered reflector 172 (e.g., frustoconical reflector) may include a second front slot 210-1b and a second rear slot 210-2b (hereinafter collectively referred to as reflector slots 210-b). Each of the first front slot 210-1a and the second front slot 210-1b (hereinafter collectively referred to as front slots 210-1) may be aligned, e.g., vertically, with each other. Similarly, each of the first rear slot 210-2a and the second rear slot 210-2b (hereinafter collectively referred to as rear slots 210-2) may be aligned, e.g., vertically, with each other. Each of the front slots 210-1 and the rear slots 210-2 (hereinafter collectively referred to as slots 210) may have any suitable dimensions for receiving the first attachment. In the third embodiment, the UV lamp 134 may be positioned horizontally within the cabinet 104 in some examples. In further examples where the inner surface of the tapered housing 170 may be operating as a reflector, instead of the tapered reflector 172 being a distinct part, the tapered reflector unit 102 may include a single front slot (not shown) and a single rear slot (not shown).

Each of the slots 210 may be extend laterally, e.g., arranged perpendicular to the longitudinal axis LF of the tapered reflector 172, or that of the tapered reflector unit 102; however, some examples may include the slots 210 being slanted at a predefined angle relative to such longitudinal axis LF. In some other examples, as illustrated in FIG. 17, the reflector slots 210-b may extend laterally up to a center of the tapered reflector 172. Such extended reflector slots 210-b may assist in positioning the first attachment within the tapered reflector 172 such as the frustoconical reflector, or the tapered reflector unit 102. Moreover, in this embodiment, the tapered reflector unit 102 may include a gap 178 between an inner surface of the housing 170 and an outer surface of the tapered reflector 172. The gap 178 may be predefined in order to assist in inserting, accommodating, or positioning the first attachment within the lumen 176 of the slotted tapered reflector 172 such as the frustoconical reflector, or that of the tapered reflector unit 102.

Figure 18:
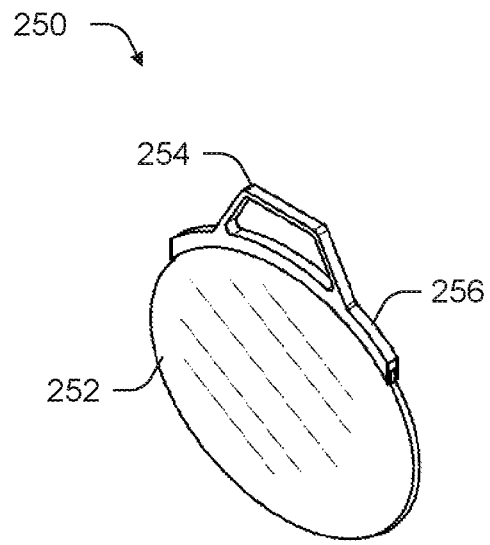
FIG. 18 is an exemplary lens attachment for the portable UV disinfector of FIG. 16, according to an embodiment of the present application.
Figure 19:
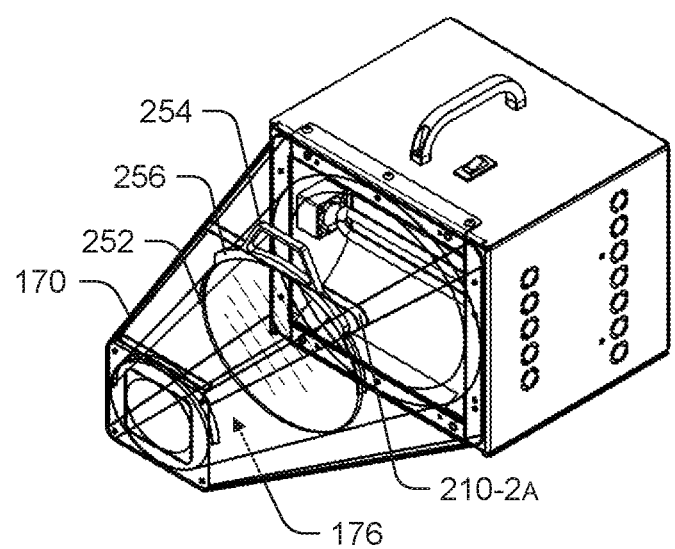
FIG. 19 is a front right perspective view of the portable UV disinfector of FIG. 16 showing the lens attachment of FIG. 18 inserted into the frustoconical reflector of FIG. 16, according to an embodiment of the present application.

In one example, the first attachment may include a lens attachment 250 as illustrated in FIG. 18. The lens attachment 250 may include a lens plate 252, a holder 254, a supporter 256 therebetween. The lens plate 252 may be attached to the holder 254 via the supporter 256. The lens plate 252 may be transparent to UV light and have any suitable shape or cross-section based on a cross-section of the tapered reflector 172. For example, the lens plate 252 may be made circular based on a circular cross-section of the tapered reflector 172. The lens attachment 250 may be configured to have any suitable thickness and size for being insertable into at least one of the front slots 210-1 and the rear slots 210-2. For example, as illustrated in FIG. 19, the lens attachment 250 may be adapted for being inserted into the rear slots 210-2. Upon being inserted, (i) the lens plate 252 may be positioned within, e.g., the lumen 176 of, the slotted tapered reflector 172, (ii) the supporter 256 may be received or disposed in the gap 178 between the housing 170 and the slotted tapered reflector 172, and (iii) the holder 254 may extend out of the first rear slot 210-2a of the housing slots 210-a and assist in placing and retrieving the lens attachment 250 in the slots 210. Similar to the lens attachment 250, other examples of the first attachment may include a shutter, an optical filter, a collimator, or any combinations thereof. In some examples, each of the front slots 210-1 and the rear slots 210-2 may be adapted to receive multiple first attachments such as multiple lens attachments. In FIGS. 8-9, FIG. 16, and FIG. 19, the housing 170 and/or the tapered reflector 172 are shown to include transparent surfaces only for the sake of explaining the related and proximate components. One having ordinary skill in the art would understand that the housing 170 and the tapered reflector 172 would be made optically impermeable to UV light based on concepts disclosed in the present application.

Figure 20:
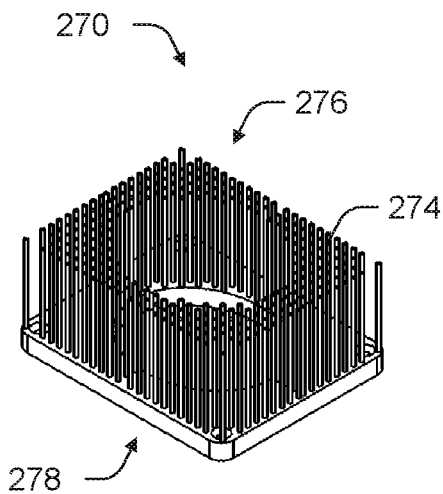
FIG. 20 is a front left perspective view of an exemplary square brush for the portable UV disinfector of FIG. 1, FIG. 2, FIG. 14, and FIG. 16, according to an embodiment of the present application.
Figure 21:
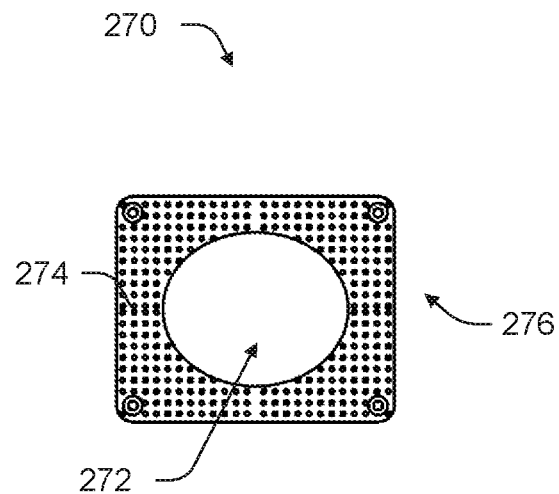
FIG. 21 is a top elevation view of the square brush of FIG. 20, according to an embodiment of the present application.
Figure 22:
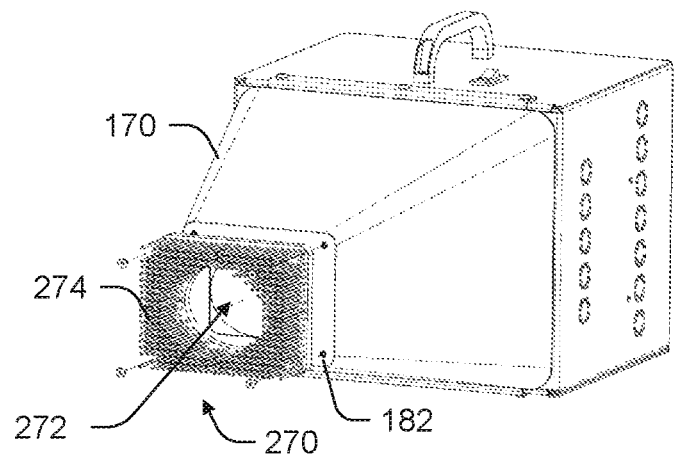
FIG. 22 is a front right perspective view of the portable UV disinfector of FIG. 1 showing the square brush of FIG. 20 being mounted thereon, according to an embodiment of the present application.

In a fourth embodiment, the distal open end 182 of the housing 170, and/or the second open end 156, may be adapted to receive or connect with a second attachment. In one example, the second attachment may be an annular brush having any suitable shapes and dimensions. For instance, as illustrated in FIG. 20 and FIG. 21, the second attachment may be a square-shaped annular brush (hereinafter referred to as square brush 270) having a central opening 272. The square brush 270 may also include bristles 274 extending away from the central opening 272. The bristles 274 may be placed on one side or surface 276 of the square brush 270 and the opposing non-bristle side 278 may be adapted for being secured to the distal open end 182. For instance, as illustrated in FIG. 22, the non-bristle side of the square brush 270 may be detachably secured or mounted to the distal open end 182 of the housing 170, or the second open end 156 of the tapered reflector unit 102, using any suitable connection mechanisms known in the art including those mentioned above. The square brush 270 may be secured in a manner that prevents light leakage from its sides.

Similarly, in another instance, as illustrated in FIG. 23 and FIG. 24, the second attachment may be a circular or round annular brush (hereinafter referred to as circular brush 280) having a central opening 272. The round or circular brush 280 may also include bristles 274 extending away from the central opening 272. The bristles 274 may be placed on one side or surface of the circular brush 280 and the opposing non-bristle side may be adapted for being secured to the distal open end 182. For instance, as illustrated in FIG. 25, the non-bristle side of the circular brush 280 may be detachably secured or mounted to the distal open end 182 of the housing 170, or the second open end 156 of the tapered reflector unit 102, using any suitable connection mechanisms known in the art including those mentioned above. The circular brush 280 may be secured in a manner that prevents light leakage from its sides.

In each of the round or circular brush 280 and the square brush 270, the central opening 272 may have any suitable cross-section or shape. For example, the central opening 272 may be circular; however, any other shapes including, but not limited to, square, rectangular, and elliptical may also be contemplated. The second attachment such as the circular brush 280 and the square brush 270 may be secured to align the central opening 272 with the distal opening 190 for allowing the UV light to pass therethrough, so that the UV light received from the tapered reflector 172 is released onto a target surface exterior to the tapered reflector unit 102, or the disinfector 100. Further, the bristles 274, or related lengths or patterns thereof, may assist in (i) preventing or limiting peripheral dispersion of the UV light away from the target surface, (ii) avoiding or limiting inadvertent UV exposure to a nearby user or the operator, (iii) defining a minimum/safe distance between a target surface and the distal opening 190 for effective disinfection, and (iv) cleaning the target surface.

Figures 26, 27:
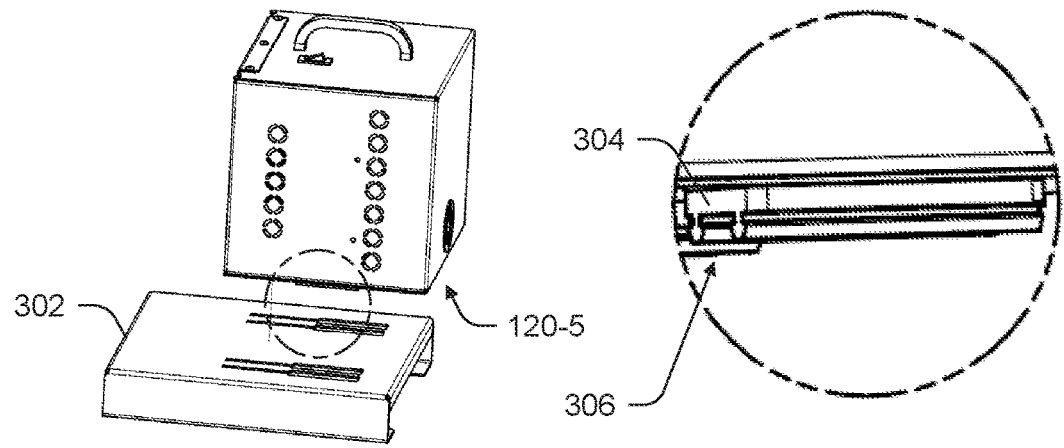
FIG. 26 is a left side perspective view of a support block for the cabinet of FIG. 3, according to an embodiment of the present application.
FIG. 27 is an exemplary connection mechanism between the cabinet of FIG. 3 and the support block of FIG. 26, according to an embodiment of the present application.
Figures 28, 29:
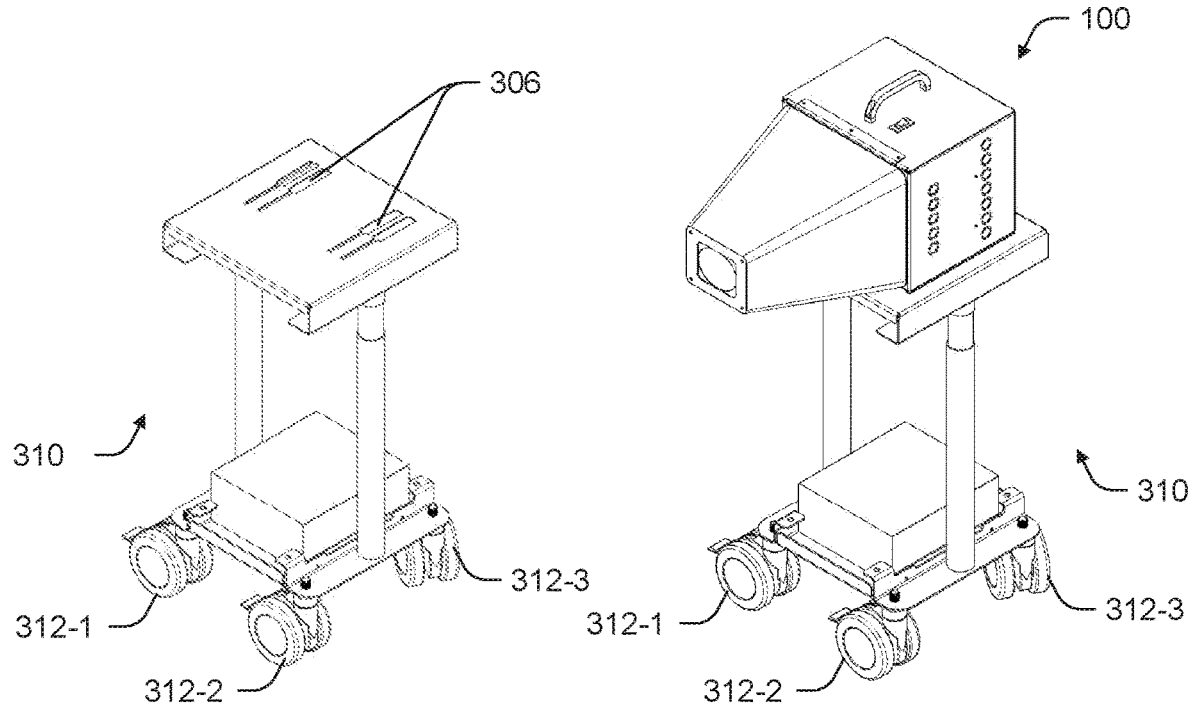
FIG. 28 is a front right perspective view of an exemplary mobile platform mounted with the support block of FIG. 26, according to an embodiment of the present application.
FIG. 29 is a front right perspective view of the portable UV disinfector of FIG. 1 mounted on the mobile platform of FIG. 26, according to an embodiment of the present application.

In further embodiments, the above described disinfector 100 may be made mobile but not handheld. Mobile may refer to a device that may be moved manually or autonomously to pass the UV light over the target surface when the disinfector 100 may be placed on a platform. Accordingly, a device such as the disinfector 100 may be placed for being easily moved in a room for surface disinfection. For this, in one embodiment, the cabinet 104 may be permanently attached, detachably secured, or formed integral to a support block 302 using any suitable connection mechanisms known in the art. For instance, as shown in FIG. 26 and FIG. 27, the bottom plate 120-5 of the cabinet 104 may include one or more clips such as a clip 304, which may be detachably secured into one or more grooves such as a groove 306 in the support block 302 being an independent part. The support block 302 may be adapted for being attached to a mobile platform 310 using any suitable connection mechanisms known in the art. In some examples, the support block 302 may be a distinct part of the mobile platform 310 formed integral thereto as shown in FIG. 28. Accordingly, the disinfector 100 may be mounted onto the mobile platform 310. As illustrated in FIG. 29, the mobile platform 310 may include wheels such as wheels 312-1, 312-2, and 312-3 (collectively wheels 312) of any suitable types known in the art including, but not limited to, omnidirectional wheels, Mecanum wheels, and caster wheels that may allow the mobile platform 310, and hence the disinfector 100, to move (sideways, forward, rotate, backward, etc.) and to be relocated with precision to any desired target position or orientation in a room. Other examples may include the mobility platform 310 being adapted as an autonomous vehicle to spatially drive the disinfector 100. The autonomous vehicle and/or motorized wheels such as the wheels 312 may be controlled by the control system, discussed above, of the disinfector 100 or a remote computing device in communication with the controller 140 over a network.

While the foregoing written description of the invention (s) enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiments, methods, and examples, but by all embodiments and methods within the scope and spirit of the present application.

The invention claimed is:

1. A handheld apparatus, comprising:
a light source;
a housing in optical communication with the light source; and
a reflector mounted within the housing, the reflector including a tapered surface, wherein the reflector includes a portion having a length inversely proportional to an angle between the tapered surface and a longitudinal axis of the reflector.

2. The handheld apparatus of claim 1, wherein the light source includes a UV source.

3. The handheld apparatus of claim 1, wherein the reflector includes a first opening and a second opening, wherein the first opening is configured to receive light from the light source for the reflector to direct the received light towards a target surface via the second opening.

4. The handheld apparatus of claim 3, wherein the first opening is at least 20% larger than the second opening.

5. The handheld apparatus of claim 1, wherein the angle ranges from 15 degrees to 75 degrees.

6. The handheld apparatus of claim 1, wherein at least one of the housing, the tapered surface, and the portion includes a textured surface.

7. The handheld apparatus of claim 1, wherein at least one of the reflector and the portion has at least one of a circular cross-section and a non-circular cross-section.

8. The handheld apparatus of claim 1, further comprising a secondary reflector in optical communication with the light source, wherein the secondary reflector is remote from the portion.

9. The handheld apparatus of claim 1, wherein the reflector or the portion includes a lumen configured to allow light from the light source to pass therethrough and towards a target surface.

10. The handheld apparatus of claim 1, further comprising a controller operating in communication with at least one of the light source, a computing device, a sensor, a camera, and a mobile platform.

11. The handheld apparatus of claim 1, further comprising a controller operating in communication with at least one of the light source, a computing device, a sensor, a camera, and a mobile platform.

12. A handheld apparatus, comprising:
a light source;
a housing in optical communication with the light source, wherein the housing includes a tapered portion remote from the light source; and
a reflector mounted within the housing, the reflector including a tapered surface, wherein the reflector includes a portion having a length inversely proportional to an angle between the tapered surface and a longitudinal axis of the reflector.

13. The handheld apparatus of claim 12, wherein the light source includes a UV source.

14. The handheld apparatus of claim 12, wherein the reflector includes a first opening and a second opening, the first opening being configured to receive light from the light source for the reflector to direct the received light towards a target surface via the second opening, wherein the tapered portion includes the second opening.

15. The handheld apparatus of claim 14, wherein the first opening is at least 20% larger than the second opening.

16. The handheld apparatus of claim 12, wherein the angle ranges from 15 degrees to 75 degrees.

17. The handheld apparatus of claim 12, wherein at least one of the housing, the tapered surface, and the portion includes a textured surface.

18. The handheld apparatus of claim 12, wherein at least one of the reflector and the portion has at least one of a circular cross-section and a non-circular cross-section.

19. The handheld apparatus of claim 12, further comprising a secondary reflector in optical communication with the light source, wherein the secondary reflector is remote from the portion.

20. The handheld apparatus of claim 12, wherein the reflector or the portion includes a lumen configured to allow light from the light source to pass therethrough and towards a target surface.

* * * * *